US005750374A

United States Patent [19]

Döbeli et al.

[11] Patent Number: 5,750,374

[45] Date of Patent: May 12, 1998

[54] PROCESS FOR PRODUCING HYDROPHOBIC POLYPEPTIDES AND PROTEINS, AND FUSION PROTEINS FOR USE IN PRODUCING SAME

[75] Inventors: Heinz Döbeli, Ziefen; Nicholas Draeger, Basel; Gerda Huber Trottman, Grindel; Peter Jakob, Reinach, all of Switzerland; Dietrich Stüber, Grenzach-Wyhlen, Germany

[73] Assignee: Hoffmann-La Roche Inc., Nutley, N.J.

[21] Appl. No.: 268,348

[22] Filed: Jun. 29, 1994

[30] Foreign Application Priority Data

Jul. 6, 1993 [EP] European Pat. Off. ............. 93110755

[51] Int. Cl.$^6$ ............................ C07K 1/00; C12P 21/00; C10P 21/06

[52] U.S. Cl. .................... 435/69.7; 530/407; 530/412; 530/415

[58] Field of Search ................... 210/198.2; 435/69.1, 435/252.3, 320.1, 69.7; 530/350, 412, 415, 407

[56] References Cited

U.S. PATENT DOCUMENTS

| 4,877,830 | 10/1989 | Döbeli et al. | 525/54.3 |
|---|---|---|---|
| 5,045,190 | 9/1991 | Carbonell et al. | 210/198.2 |
| 5,047,513 | 9/1991 | Döbeli et al. | 530/412 |
| 5,284,933 | 2/1994 | Döbeli et al. | 530/350 |
| 5,310,663 | 5/1994 | Döbeli et al. | 435/69.7 |
| 5,416,007 | 5/1995 | Charette | 435/68.1 |

FOREIGN PATENT DOCUMENTS

| 11303/92 | 2/1992 | Australia . |
| 207 044 | 6/1986 | European Pat. Off. . |
| 212 532 | 6/1986 | European Pat. Off. . |
| 289 110 | 11/1988 | European Pat. Off. . |
| 331 961 | 9/1989 | European Pat. Off. . |
| 353 823 | 2/1990 | European Pat. Off. . |
| 484 787 | 5/1992 | European Pat. Off. . |
| 91/19810 | 12/1991 | WIPO . |
| 93/03376 | 2/1993 | WIPO . |

OTHER PUBLICATIONS

Kang et al., Nature 325, 733–736 (1987).
Barr et al., Vaccine 5(2), 90–101 (1987).
Chiodi et al., J. Med. Virology 23(1), 1–9 (1987).
Darnell et. al., Molecular Cell Biology. pp. 945–949 (1986).
Sambrook et al., Molecular Cloning. 2nd. ed., 1989, 17.29–17.33.
Abstract for Document 484 787.
Muesing, Mark A., et al., *Nature*, 313:450–458 (1985).
Houchuli and Döbeli, *Biol. Chem.*, Hoppe-Seyler, vol. 368, p. 748 (1987). (Abstract).
Basu et al., "Expression of Growth Hormone–Releasing Factor Analog Leucine–27 GRF 1–44 Hydroxyl in *Escherichia–coli* Purification and Characterization of the Expressed Protein," Arch Biochem Biophys 286(2). 1991. 638–644.
Kobayashi et al. "The Complete Amino Acid Sequence of Growth Hormone of the Bullfrog *Rana–catesbeiana*", Biochim Biophys Acta 1078 (3). 1991. 383–387.
Cassidy et al. "*Asparaaginyl deamidation*—Methylation of Rat Ventricular Myosin Light Chains", J Mol Cell Cardiol 23 (5). 1991. 589–602.
Jarrett et al. "*Amyloid fibril* Formation Requires a Chemically Discriminating Nucleation Event Studies of an Amyloidogenic Sequence from the Bacterial Protein OSMB", Biochemistry 31 (49). 1992. 12345–12352.
Currie et al., "Immunolocalization of Alzheimer Beta Amyloid Peptide Precursor to Cellular Membranes in Baculovirus Expression System," J Neurosci Res 30 (4). 1991. 687–698.
Warren et al., "Comparative Purification of Recombinant HIV–1 and HIV–2 Reverse Transcriptase Preparation of Heterodimeric Enzyme Devoid of Unprocessed Gene Product," Protein Expression Purif 3 (6). 1992. 479–487.

*Primary Examiner*—Vasu S. Jagannathan
*Assistant Examiner*—Brian K. Lathrop
*Attorney, Agent, or Firm*—George W. Johnston; William H. Epstein; John P. Parise

[57] ABSTRACT

Methods are disclosed for the production and purification of hydrophobic fusion proteins production and purification of said hydrophobic polypeptides, proteins or peptides. Homogeneous monomeric β-amyloid peptide and tests for screening amyloid toxicity-inhibiting drugs using this monomeric β-amyloid peptide relate to these fusion proteins.

8 Claims, 7 Drawing Sheets

```
         XhoI
   1 CTCGAGAAATCATAAAAAATTTATTTGCTTTGTGAGCGGATAACAATTATAATAGATTCA

EcoRI
  61 ATTGTGAGCGGATAACAATTTCACACAGAATTCATTAAAGAGGAGAAATTAACTATGAGA
                                                              MetArg

121 GGATCGCATCACCATCACCATCACGGATCTAACGCGAACCCGAACGCGAACCCGAACGCG
     GlySerHisHisHisHisHisHisGlySerAsnAlaAsnProAsnAlaAsnProAsnAla

181 AACCCGAACGCGAACCCGAACGCGAACCCGAACGCGAACCCGAACGCGAACCCGAACGCG
     AsnProAsnAlaAsnProAsnAlaAsnProAsnAlaAsnProAnsAlaAsnProAsnAla

241 AACCCGAACGCGAACCCGAACGCGAACCCGAACGCGAACCCGAACGCGAACCCGAACGCG
     AsnProAsnAlaAsnProAsnAlaAsnProAsnAlaAsnProAsnAlaAsnProAsnAla

301 AACCCGAACGCGAACCCGAACGCGAACCCGAACGCGAACCCGAACGCGAACCCGAACGCG
     AsnProAsnAlaAsnProAsnAlaAsnProAnsAlaAsnProAsnAlaAsnProAsnAla

BglII
 361 AACCCGAACGCGAACCCGAGATCTATGGATGCGGAGTTCGGACATGATTCAGGCTTCGAA
     AsnProAsnAlaAsnProArgSerMetAspAlaGluPheGlyHisAspSerGlyPheGlu
                             1                                 11

421 GTCCGCCATCAAAAACTGGTGTTCTTTGCAGAAGATGTGGGTTCAAACAAAGGTGCCATC
     ValArgHisGlnLysLeuValPhePheAlaGluAspValGlySerAsnLysGlyAlaIle
                             21                                31

HindIII
 481 ATTGGACTCATGGTGGGTGGCGTTGTCATAGCATAAGCTT    520 (Seq. ID No:7)
     IleGlyLeuMetValGlyGlyValValIleAla               (Seq. ID No:6)
                                     41
```

```
     XhoI
  1  CTCGAGAAATCATAAAAAATTTATTTGCTTTGTGAGCGGATAACAATTATAATAGATTCA

EcoRI
 61  ATTGTGAGCGGATAACAATTTCACACAGAATTCATTAAAGAGGAGAAATTAACTATGAGA
                                                            MetArg

121  GGATCGCATCACCATCACCATCACGGATCTAACGCGAACCCGAACGCGAACCCGAACGCG
     GlySerHisHisHisHisHisHisGlySerAsnAlaAsnProAsnAlaAsnProAnsAla

181  AACCCGAACGCGAACCCGAACGCGAACCCGAACGCGAACCCGAACGCGAACCCGAACGCG
     AsnProAsnAlaAsnProAsnAlaAsnProAsnAlaAsnProAsnAlaAsnProAsnAla

241  AACCCGAACGCGAACCCGAACGCGAACCCGAACGCGAACCCGAACGCGAACCCGAACGCG
     AsnProAsnAlaAsnProAsnAlaAsnProAsnAlaAsnProAsnAlaAsnProAsnAla

301  AACCCGAACGCGAACCCGAACGCGAACCCGAACGCGAACCCGAACGCGAACCCGAACGCG
     AsnProAsnAlaAsnProAsnAlaAsnProAsnAlaAsnProAsnAlaAsnProAsnAla

BglII
361  AACCCGAACGCGAACCCGAGATCTATGGATGCGGAGTTCGGACATGATTCAGGCTTCGAA
     AsnProAsnAlaAsnProArgSerMetAspAlaGluPheGlyHisAspSerGlyPheGlu
                            1                                 11

421  GTCCGCCATCAAAAACTGGTGTTCTTTGCAGAAGATGTGGGTTCAAACAAAGGTGCCATC
     ValArgHisGlnLysLeuValPhePheAlaGluAspValGlySerAsnLysGlyAlaIle
                         21                                  31

HindIII
481  ATTGGACTCATGGTGGGTGGCGTTGTCATAGCATAAGCTT   520  (Seq.ID No: 9)
     IleGlyLeuMetValGlyGlyValValIleAla                (Seq.ID No:10)
       35                    41

[M35E]:  GAG      [M25L]:  CTG      [M35Q]:  CAG      [M35S]:  TCT
              Glu               Leu               Gln               Ser
              35                35                35                35
```

PROCESS FOR PRODUCING HYDROPHOBIC POLYPEPTIDES AND PROTEINS, AND FUSION PROTEINS FOR USE IN PRODUCING SAME

FIELD OF THE INVENTION

The subject invention relates to a process for producing hydrophobic polypeptides, proteins and peptides, and fusion proteins for use in producing same.

BACKGROUND OF THE INVENTION

The ability to prepare hybrid genes by gene technology opens up new routes for working-up recombinant proteins. By linking the coding gene sequence of a desired protein with the coding gene sequence of a protein fragment having a high affinity for a ligand (affinity peptide), it is possible to produce a fusion protein and purify a desired recombinant protein in the form of the fusion protein in one step through the use of the affinity peptide. By site-directed mutagenesis, it is also possible to introduce specific chemical or enzymatic cleavage sites at the point of linkage of the affinity peptide and the desired recombinant protein, so that after purification of the fusion protein by means of a suitable affinity resin, the desired recombinant protein can be recovered by chemical or enzymatic cleavage.

However, recovering the desired recombinant protein may turn out to be extremely difficult when the desired recombinant protein also contains such chemical or enzymatic cleavage sites in its amino acid sequence. In such cases, the desired recombinant protein ends up being rapidly degraded.

In order to inhibit this degradation, the present invention provides fusion proteins and processes which allow selective cleavage at a specific chemical or enzymatic cleavage site without affecting the desired recombinant protein. Methods of the present invention are specifically applicable for production of hydrophobic polypeptides, proteins or peptides.

SUMMARY OF THE INVENTION

The present invention is concerned with fusion proteins of the formula:

A—B—C wherein A is a bulky hydrophilic peptide, B is a selective cleavage site, and C is a desired hydrophobic polypeptide, protein or peptide.

The term "bulky hydrophilic peptide" is used in connection with fusion proteins in accordance with the invention and relates to hydrophilic peptides which are characterized by their size and the content of hydrophilic amino acids giving rise to a well structured domain.

The bulky hydrophilic peptide A of the fusion proteins in accordance with the invention serves a dual function: (a) to facilitate high expression of the fusion proteins, and (b) to expose cleavage site B to the mobile phase on a hydrophobic matrix column. Preferred bulky hydrophilic peptides of the fusion proteins in accordance with the invention are those with the peptide sequence of the formula (NANP)x wherein x is 10–40, with 19 being most preferred.

Selective cleavage sites include chemical and enzymatic cleavage sites.

Suitable selective enzymatic cleavage sites include (i) the amino acid sequences -(Asp)$_n$-Lys-, wherein n signifies 2, 3 or 4, or -Ile-Glu-Gly-Arg- which can be specifically recognized by the proteases enterokinase and coagulation factor $X_a$, respectively, (ii) an arginine residue or a lysine residue cleaved by trypsin, (iii) a lysine residue cleaved by lysyl endopeptidase, and (iv) a glutamine residue cleaved by V8 protease.

Suitable selective chemical cleavage sites include (i) tryptophan residues cleaved by 3-bromo-3-methyl-2-(2-nitrophenylmercapto)-3H-indole, (ii) cystein residues cleaved by 2-nitroso-5-thiocyano benzoic acid, (iii) the amino acid dipeptides Asp-Pro or Asn-Gly which can be cleaved by acid and hydroxylamine, respectively, and preferably, (iv) a methionine residue which is specifically cleaved by cyanogen bromide (CNBr).

The term "hydrophobic polypeptide, protein or peptide" is used in connection with the fusion proteins in accordance with the invention and relates to hydrophobic polypeptides, proteins or peptides which elute from reverse phase HPLC columns at concentrations between about 30% and about 60%, preferably around about 40% organic solvent in aqueous buffer, e.g. at a concentration of higher than about 40% ethanol in aqueous buffer.

Hydrophobic polypeptides, proteins or peptides include, for example, surface antigens, lymphokine receptors, HIV-1 and HIV-2 envelope and structure proteins, hepatitis C envelope and structure proteins, and any peptide with membrane anchor sequences. Preferred hydrophobic polypeptides, proteins or peptides are β-amyloid peptide (bA4-amyloid) having the sequence:

DAEFRHDSGYEVHHQKLVFFAEDVGSNK-GAIIGLMVGGVVIA (Seq ID No: 1)

point mutations of bA4-peptide having at position 35 a leucine (Seq ID No:3), serine (Seq ID No:4), glutamine (Seq ID No:5) or glutamic acid (Seq ID No:6) residue instead of a methionine or methionine sulfoxide residue and HIV-1 envelope peptide having the sequence:

RILAVERYLKDQQLLGIWGCSGKLICTTAVPWNAS (Seq ID No: 11)

Bulky hydrophilic peptides and the selective cleavage sites of fusion proteins in accordance with the invention can be linked either to the amino terminal amino acid or to the carboxy terminal amino acid of the hydrophobic polypeptide, protein or peptide.

The fusion proteins in accordance with the present invention can optionally contain specific sequences that preferably bind to an affinity carrier material. Examples of such sequences are sequences containing at least two adjacent histidine residues (see in this respect European Patent Application Publication No. 282 042 corresponding to U.S. Pat. Nos. 5,284,933 and 5,310,663, the contents of each being herein incorporated by reference). Such sequences bind selectively to nitrilotriacetic acid nickel chelate resins (Hochuli and Döbeli, Biol.Chem. Hoppe-Seyler 368, 748 (1987); European Patent No. 253 303, corresponding to U.S. Pat. Nos. 4,877,830 and 5,047,513, the contents of each being herein incorporated by reference). Fusion proteins of the present invention which contain such a specific sequence can, therefore, be separated selectively from remaining polypeptides. The specific sequence can be linked either to the amino acid sequence of the bulky hydrophilic peptide or the amino acid sequence of the hydrophobic polypeptide, protein or peptide.

The present invention is also concerned with genes which code for these fusion proteins, expression vectors which contain these genes, microorganisms transformed with these expression vectors as well as a process for the preparation of said genes, expression vectors and transformed microorganisms.

Preparation of the fusion proteins in accordance with the invention can be effected according to methods of recombinant DNA technology described in the literature. Preferably, a nucleotide sequence coding for the desired hydrophobic polypeptide, protein or peptide is firstly synthesized and this is then linked with a nucleotide sequence coding for the bulky hydrophilic peptide and the selective cleavage site.

Incorporation of the thus-obtained hybrid gene into expression vectors can be effected using methods known to the skilled artisan. In this context, reference can be made to the textbooks of Maniatis et al. ("Molecular Cloning", Cold Spring Harbor Laboratory, 1982) and Sambrook et al. ("Molecular Cloning-A Laboratory Manual", 2nd. ed., Cold Spring Harbor Laboratory, 1989), the contents of both being herein incorporated by reference.

Methods for the expression of fusion proteins in accordance with the invention are also known to the skilled artisan, and are described in detail in the aforementioned textbooks. They embrace the following procedures:

a) transformation of a suitable host organism, advantageously E. coli, with an expression vector in which an aforementioned hybrid gene is operatively bonded to an expression control sequence;

b) cultivation of the thus-obtained host organism under suitable growth conditions; and c) extraction and isolation of the desired fusion protein from the host organism.

Host organisms include gram-negative and gram-positive bacteria, for example *E. coli* and *B. subtilis* strains. *E. coli* strain M15 is an especially preferred host organism of the present invention. Apart from the above-mentioned *E. coli* strain there can, however, also be used other generally accessible *E. coli* strains, for example *E. coli* 294 (ATCC No.3144), *E. coli* RR1 (ATCC No.31343) and *E. coli* W3110 (ATCC No. 27325).

Fusion proteins in accordance with the present invention allow selective cleavage at a specific chemical or enzymatic cleavage site without affecting the desired hydrophobic polypeptide, protein or peptide. Diffusion of the desired hydrophobic polypeptide, protein or peptide into the solid phase of a hydrophobic matrix column enables orientation of the fusion proteins in accordance with the present invention so as to hide the desired hydrophobic polypeptide, protein or peptide. The bulky hydrophilic peptide, on the other hand, exposes the selective cleavage site to the mobile aqueous phase. This allows for removal of the bulky hydrophilic peptide by selective cleavage, leaving only the desired hydrophobic polypeptide, protein or peptide bound to the column. The desired hydrophobic polypeptide, protein or peptide can then be eluted by addition of organic solvents.

Hence, the present invention also provides a process for the production and purification of a desired hydrophobic polypeptide protein or peptide, which process comprises the steps of:

a) passing an aqueous solution containing a fusion protein in accordance with the present invention through a hydrophobic matrix column, b) flushing the column with a solution containing a cleavage reagent or an enzyme, and c) removing the resulting desired hydrophobic polypeptide, protein or peptide with an aqueous water miscible solvent.

Hydrophobic matrix columns include cyanopropyl, cyclohexyl, phenyl, octyl or octadecyl group bonded silica matrix columns. In the preferred practice of the invention, RP - 18 (octadecyl bound silica microparticle column) under reverse phase high performance liquid chromatography (HPLC) conditions is used.

Prior to the loading with the inventive fusion protein, the hydrophobic matrix column is conveniently equilibrated with an aqueous buffer. The equilibration buffer may contain a denaturing agent or a chaotropic agent, for example guanidine-HCl, urea or a detergent, e.g. TRITON. Addition of such a denaturing agent, chaotropic agent or detergent permits problem-free operation even with the subject fusion proteins which tend to be extremely difficult to solubilize in aqueous solution.

The fusion protein in accordance with the present invention may be applied onto a hydrophobic matrix column in aqueous buffer which may also contain a denaturing agent or a detergent, for example guanidine-HCl, urea or TRITON.

Cleavage is performed by flushing the column with an aqueous buffer containing a cleavage reagent or an enzyme. Optimal buffer composition depends on the cleavage reagent or enzyme used and is conveniently determined on a case-by-case basis.

Elution of the desired hydrophobic polypeptides, proteins or peptides may be carried out using a gradient of an aqueous water miscible solvent. Suitable water miscible solvents for this purpose include alkanols, such as n-propanol, 2-propanol, ethanol, methanol, tert- butanol, or cyclic ethers, such as dioxane. Optimal elution conditions depend on desired hydrophobic polypeptide, protein or peptide to be purified, hydrophobic matrix, column dimensions etc., and are conveniently determined on a case-by-case basis.

The aforementioned process for production and purification of a desired hydrophobic polypeptide protein or peptide may also be carried out batchwise. The fusion protein in accordance with the present invention is then absorbed to a hydrophobic matrix in aqueous buffer. Cleavage is performed by incubating the hydrophobic matrix with an aqueous buffer containing the cleavage reagent or the enzyme. The desired hydrophobic polypeptide can be obtained by incubating the hydrophobic matrix with the aqueous water miscible solvent after removal of the cleavage reagent or enzyme and the bulky hydrophilic peptides.

In a preferred specific embodiment of the present invention, a novel process allowing production and purification of a desired hydrophobic polypeptide, protein or peptide is employed to purify β-amyloid peptides in monomeric form to homogeneity.

The specific process for producing a monomeric β-amyloid peptide as homogeneous peptide comprises the following steps in combination:

a) passing an aqueous solution containing a fusion protein in accordance with the present invention, wherein the desired hydrophobic peptide is the β-amyloid peptide, through a hydrophobic matrix column, b) flushing the column with a solution containing a cleavage reagent or an enzyme, c) obtaining monomeric β-amyloid peptide by elution with an aqueous water miscible solvent, d) diluting the monomeric β-amyloid peptide with distilled water followed by lyophilization, and e) optionally, if desired, purifying the monomeric β-amyloid peptide after lyophilization to achieve ultimate homogeneity.

In performing the specific process for producing monomeric β-amyloid peptide as a homogeneous peptide, the solution containing the fusion protein (wherein the desired hydrophobic peptide is a β-amyloid peptide, preferably in aqueous buffer containing a denaturing agent, e.g. guanidine-HCl or urea), is passed through the hydrophobic matrix column. In the preferred practice, RP-18 (octadecyl bound silica micro-particle column) under reverse phase high performance liquid chromatography (HPLC) conditions is used. Further suitable columns for this purpose include cyanopropyl, cyclohexyl, phenyl or octyl-columns (Bead size from about 5–30 mm). These columns are commercely, available from Vydac or Macherey-Nagel under the trademarks VYDAC or NUCLEOSIL. Cleavage is performed by flushing the column with an aqueous buffer containing a cleavage reagent or an enzyme. In the preferred practice, cleavage is performed by flushing the column with cyanogen bromide in an aqueous buffered water miscible solvent. The elution of the monomeric β-amyloid peptide is carried out using a gradient of an aqueous water miscible solvent, preferably an ethanol gradient. The monomeric β-amyloid peptide is immediately diluted with distilled water, e.g., by dropping the eluate into a container containing water, and is then lyophilized. If desired, the monomeric β-amyloid peptide may be purified by known methods, e.g. by preparative gel electrophoresis or by size exclusion chromatography, after lyophilization in order to achieve ultimate homogeneity. In the preferred practice preparative non-denaturing gel electrophoresis (for the isolation of large quantities of monomeric β-amyloid peptide) and gel filtration under HPLC conditions (for the isolation of small quantities of monomeric β-amyloid peptide) is applied.

The present invention also relates to the pure and homogeneous, toxic monomeric β-amyloid peptides obtained by the novel process.

The β-amyloid peptides in accordance with the present invention may be used for screening Alzheimer drugs.

The novel process allowing production and purification of a desired hydrophobic polypeptide, protein or peptide is also employed to purify HIV-1 envelope peptide Seq ID No: 11 to homogeneity using analogous conditions as those used for the purification of monomeric β-amyloid peptide (Example 7).

The HIV-1 envelope peptide Seq ID No: 11 obtained by the novel process may be used in diagnosing HIV infections.

BRIEF DESCRIPTION OF THE FIGURES

The invention has been described in general terms hereinabove. The following Examples are intended to illustrate details of the invention, without thereby it in any manner. The following Examples can be understood better when read in conjunction with the accompanying Figures. The following symbols appear in these Figures:

'N25OPSN25OP29' represents the regulatable promoter/operator element N25OPSN25OP29, 'RBSII' represents the synthetic ribosomal binding site RBSII; '[His]6', '[NANP] 19' and 'amy' represent the genes encoding the 6xHis-NANP-amyloid fusion proteins of this invention; 'bla', 'cat', 'lacI' and 'neo' represent the genes for beta-lactamase, chloramphenicol acetyltransferase, lac repressor and neomycin phosphotransferase, respectively; 'to', 'TE' and 'T1' represent transcriptional terminators $t_o$ of phage lambda, TE of phage T7 and T1 of the *E. coli* rrnB operon; 'repl.' represents the replication regions of plasmids pBR322 and pREP4.

FIGS. 6A and 6B—Illustrate bA4 analysis by non-denaturing agarose gel electropheresis. Analysis was performed with "Serum Protein Electrophoresis system Paragon" from Beckman according to the recommendations of the supplier. 8 µg (in 2 µl H$_2$O) of peptide each were applied. Staining was with Coomassie brilliant blue for 3 h and destaining with 10% acetic acid, 45% methanol and 45% water. Samples were prepared in distilled water immediately before the experiment (f) or allowed to age for 2 days (a). The samples tested are given in the list below.

| | FIG. 6A (gel a) | | FIG. 6B (gel b) |
|---|---|---|---|
| lane 1 | human bA4 wash 1 f | lane 1 | M35S bA4 wash 1 f |
| lane 2 | human bA4 wash 2 f | lane 2 | M35S bA4 wash 2 f |
| lane 3 | human bA4 wash 3 f | lane 3 | M35S bA4 wash 3 f |
| lane 4 | human bA4 wash 4 f | lane 4 | M35S bA4 wash 4 f |
| lane 5 | human bA4 wash 4 a | lane 5 | M35S bA4 wash 4 a |
| lane 6 | Standard BSA 2 mg | lane 6 | Standard BSA 10 mg |
| lane 7 | M35L bA4 wash 1 f | lane 7 | M35Q bA4 wash 1 f |
| lane 8 | M35L bA4 wash 2 f | lane 8 | M35Q bA4 wash 2 f |
| lane 9 | M35L bA4 wash 3 f | lane 9 | M35Q bA4 wash 3 f |
| lane 10 | M35L bA4 wash 3 a | lane 10 | rat bA4 |

Fractions of 250 ml each were collected and analyzed by non-denaturing electrophoresis. Lane 1: bA4 applied onto the column. Lanes 2 to 10: peak fractions.

The marker proteins used to determine the size of bA4 were:

serum albumin (MW=65000; retention time=19.89 min), ovalbumine (MW=45000; retention time=20.10 min), lactalbumin (MW=14200; retention time=21.43 min) and insulin (MW=5734; retention time=21.68 min).

The retention time of 22.54 min. points to a monomer with a MW of about 4500 daltons. This is in agreement with light-scattering data and ultracentrifugation experiments by the Yphantis method (D. A. Yphantis, Annals of the N.Y. Acad.Sci. 88, 586–601 [1960], the contents of which are herein incorporated by reference).

DETAILED DESCRIPTION OF THE INVENTION

The subject invention will now be described in terms of its preferred embodiments. These embodiments are set forth to aid in the understanding of the invention, but are not to be construed as limiting.

EXAMPLE 1

Figure 1:
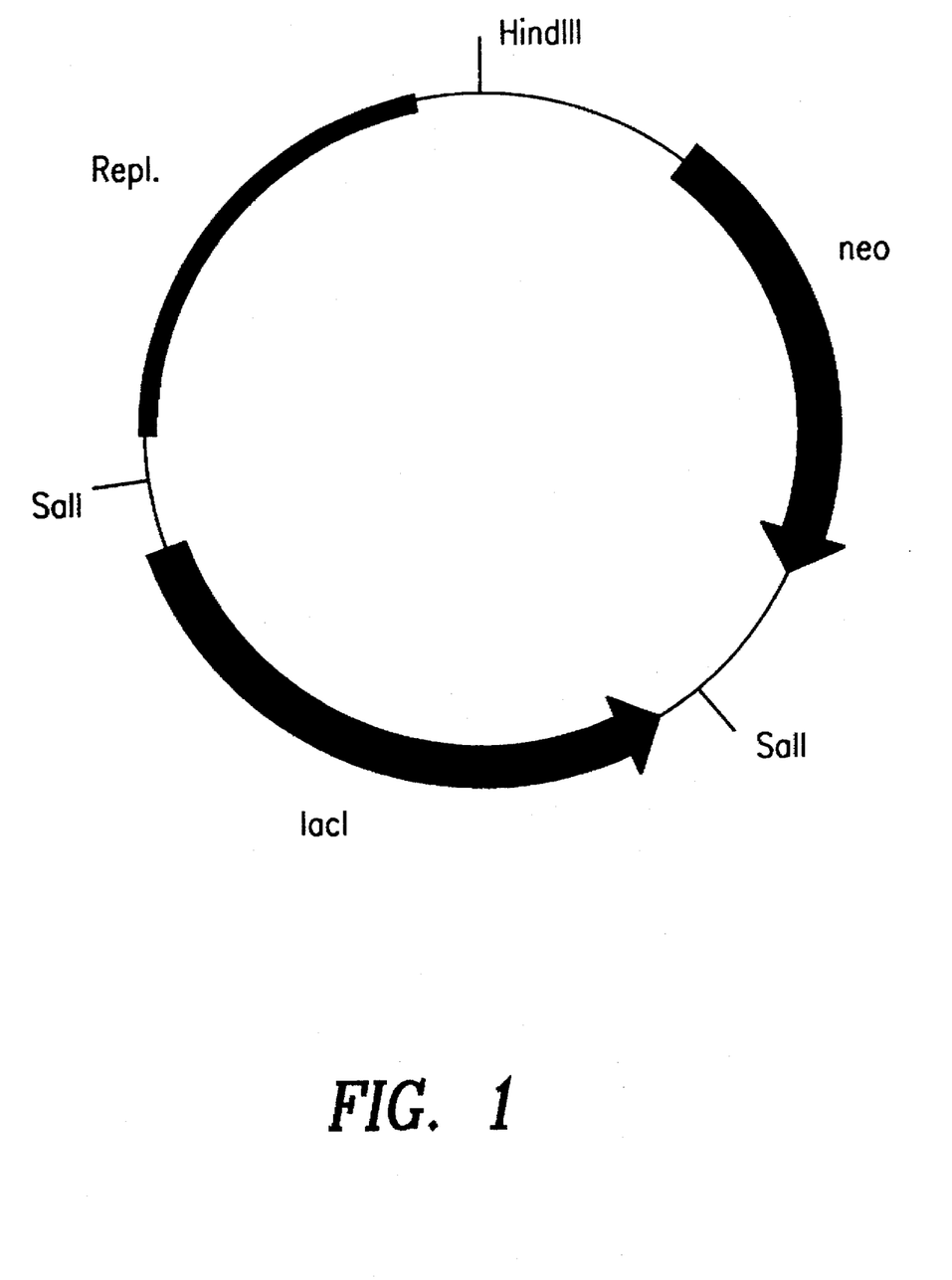
FIG. 1—A schematic drawing of the plasmid pREP4.
Figure 2:
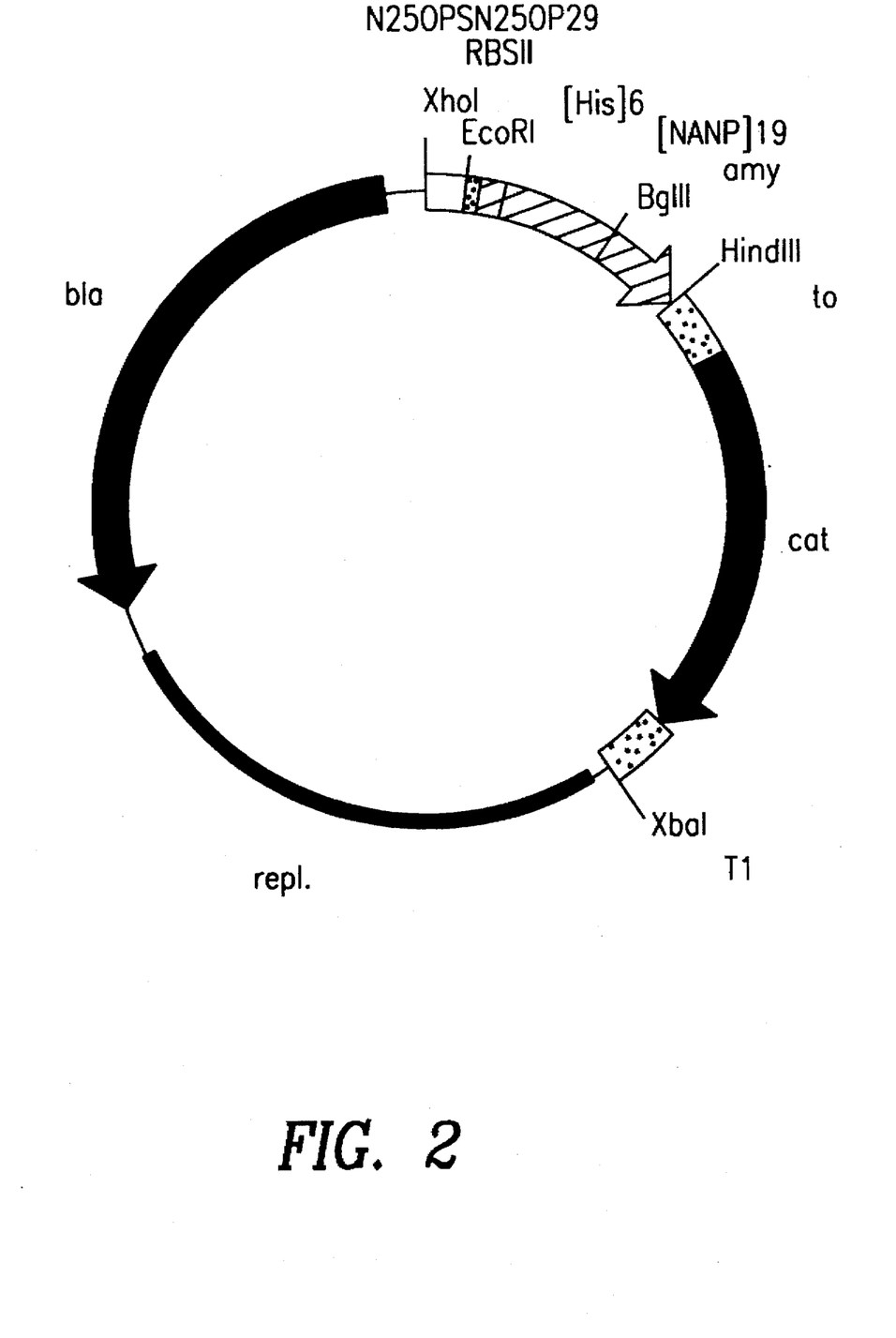
FIG. 2—A schematic drawing of the plasmid p6xHis-NANP-Met-Amy.
Figure 3:
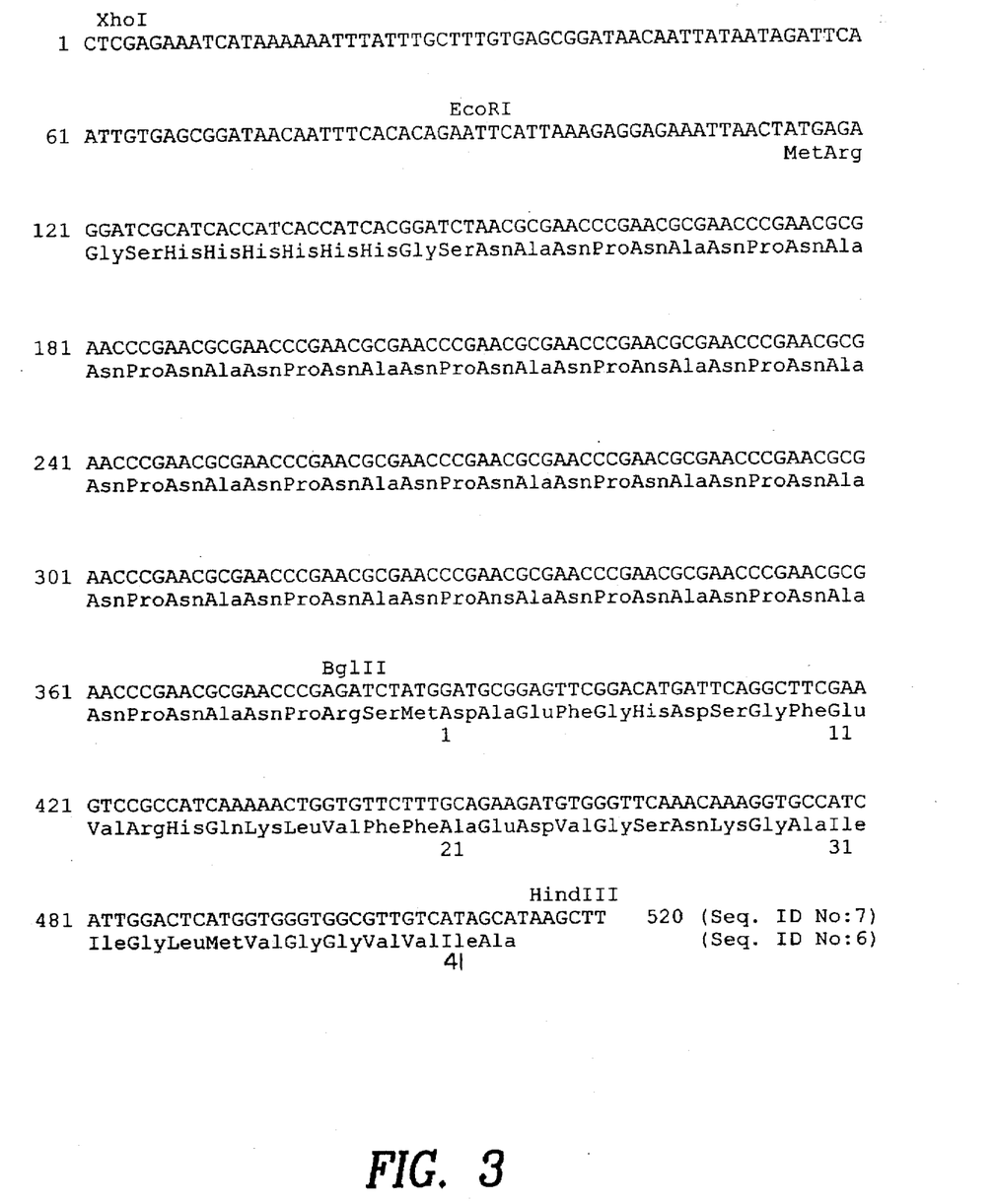
FIG. 3—A sequence listing displaying that part of the nucleotide sequence of plasmid p6xHis-NANP-Met-Amy (Seq ID No: 7) which encodes fusion protein 6xHis-NANP-Met-Amy (Seq ID No: 8). In this sequence, recognition sequences of some of the restriction enzymes depicted in FIG. 2 are indicated. The amino acid sequence represents in three-letter code the sequence of fusion protein 6xHis-NANP-Met-Amy, amino acids corresponding to the bA4-peptide are numbered.

Expression Plasmid Used For the Preparation of the Fusion Protein 6xHis-NANP-Met-Amy The expression plasmid p6xHis-NANP-Met-Amy (see FIGS. 2 and 3) was used for the preparation of the fusion protein 6xHis-NANP-Met-Amy. E. coli M15 cells transformed with plasmids pREP4 and p6xHis-NANP-Met-Amy were deposited in accordance with the Budapest Treaty at the Deutsche Sammlung von Mikroorganismen (DSM) in Braunschweig, BRD, on May 18, 1993, under the accession number DSM 8310.

EXAMPLE 2

Figure 4:
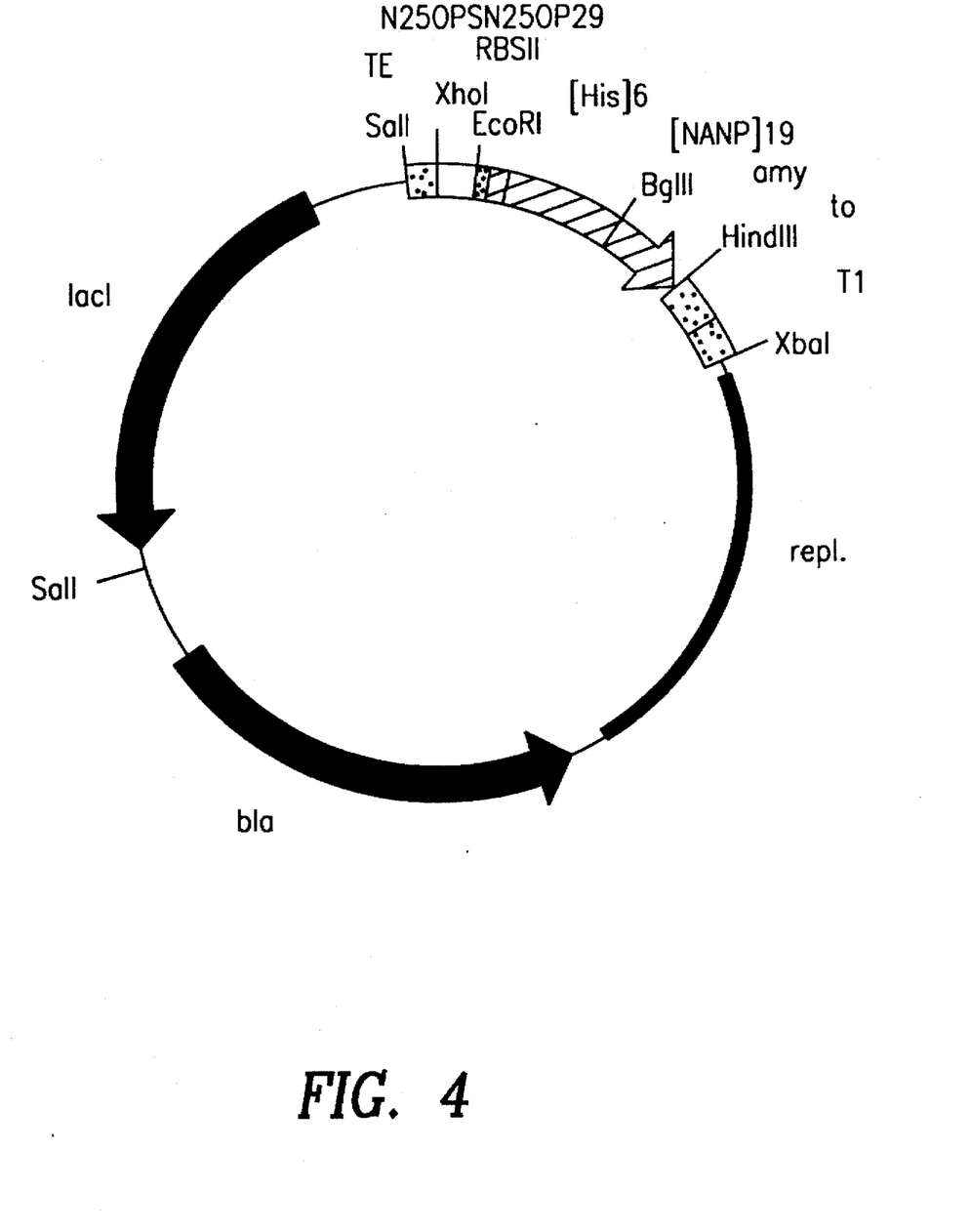
FIG. 4—A schematic drawing of plasmid pB/E1-6xHis-NANP-Met-huAmy.
Figure 5:
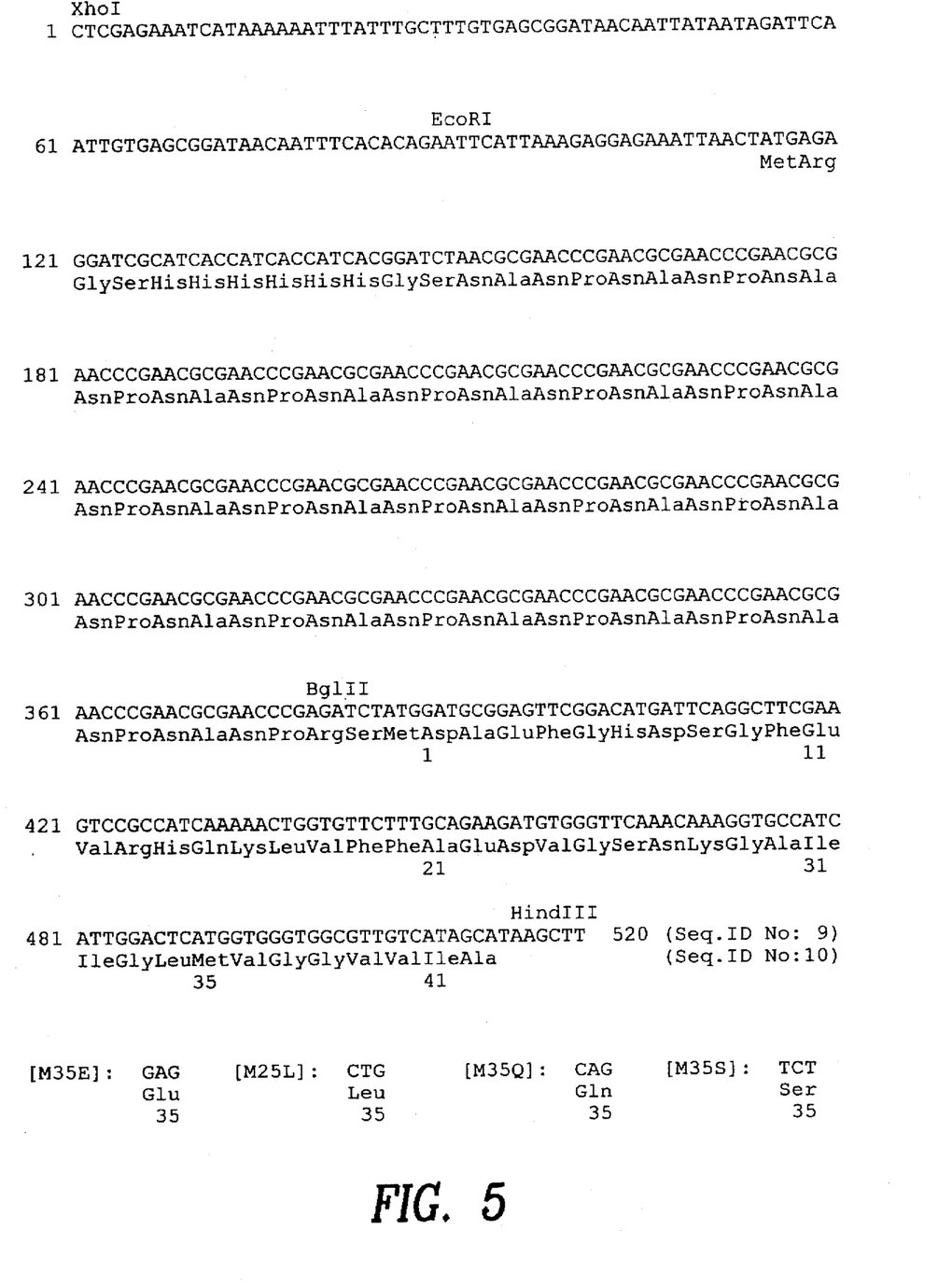
FIG. 5—A sequence listing displaying that part of nucleotide sequence of plasmid pB/E1-6xHis-NANP-Met-huAmy (Seq ID No: 9) which encodes fusion protein 6xHis-NANP-Met-huAmy (Seq ID No: 10). In this sequence, recognition sequences of some of the restriction enzymes depicted in FIG. 4 are indicated. The amino acid sequence represents in the three-letter code the sequence of fusion protein 6xHis-NANP-Met-huAmy, amino acids corresponding to the bA4-peptide are numbered. The lower part of FIG. 5 displays nucleotide sequences and encoded amino acids by which plasmid pB/E1-6xHis-NANP-Met-huAmy [M35E], which encodes fusion protein 6xHis-NANP-Met-huAmy[M35E], plasmid pB/E1-6xHis-NANP-Met-huAmy [M35L], which encodes fusion protein 6xHis-NANP-Met-huAmy[M35L], plasmid pB/E1-6xHis-NANP-Met-huAmy [M35Q], which encodes fusion protein 6xHis-NANP-Met-huAmy[M35Q], and plasmid pB/E1-6xHis-NANP-Met-huAmy[M35S], which encodes fusion protein 6xHis-NANP-Met-huAmy[M35S], differ from plasmid pB/E1-6xis-NANP-Met-huAmy.

Expression Plasmid Used For the Preparation of the Fusion Protein 6xHis-NANP-Met-huAmy The expression plasmid pB/E1-6xHis-NANP-Met-huAmy (see FIGS. 4 and 5) was used for the preparation of the fusion protein 6xHis-NANP-Met-huAmy. E. coli M15 cells transformed with plasmids pREP4 and pB/E1-6xHis-NANP-Met-huAmy were deposited in accordance with the Budapest Treaty at the Deutsche Sammlung von Mikroorganismen (DSM) in Braunschweig, BRD, on May 18, 1993, under the accession number DSM 8311.

EXAMPLE 3

Expression Plasmids Used for the Preparation of the Fusion Proteins 6xHis-NANP-Met-huAmy [M35L], 6xHis-NANP-Met-huAmy[M35Q], 6xHis-NANP-Met-huAmy[M35S], And 6xHis-NANP-Met-huAmy [M35E]

The expression plasmids pB/E1-6xHis-NANP-Met-huAmy[M35L], pB/E1-16xHis-NANP-Met-huAmy[M35Q], pB/E1-6xHis-NANP-Met-huAmy[M35S] and PB/E1-6xHis-NANP-Met-huAmy[M35E], which differ from plasmid pB/E1-6xHis-NANP-Met-huAmy only in the nucleotides encoding amino acid 35 of the bA4 amyloid peptide (see FIG. 5), were used for the preparation of the fusion proteins 6xHis-NANP-Met-huAmy[M35L], 6xHis-NANP-Met-huAmy[M35Q], 6xHis-NANP-Met-huAmy [M35S] and 6xHis-NANP-Met-huAmy[M35E], respectively. E. coli M15 cells transformed with plasmids pREP4 and pB/E1-6xHis-NANP-Met-huAmy[M35L], pREP4 and pB/E1-6xHis-NANP-Met-huAmy[M35Q], pREP4 and pB/E1-6xHis-NANP-Met-huAmy[M35S] and pREP4 and pB/E1-6xHis-NANP-Met-huAmy[M35E]], respectively, were deposited in accordance with the Budapest Treaty at the Deutsche Sammlung von Mikroorganismen (DSM) in Braunschweig, BRD, on May 18, 1993, under the accession numbers DSM 8313, DSM 8314, DSM 8315 and DSM 8312, respectively.

EXAMPLE 4

Fermentation and Purification of Fusion Proteins

Fermentation

Plasmids p6xHis-NANP-Met-Amy, pB/E1-6xHis-NANP-Met-huAmy, pB/E1 6xHis-NANP-Met-huAmy [M35L], pB/E1-6xHis-NANP-Met-huAmy[M35Q] pB/E1-6xHis-NANP-Met-huAmy [M35S] and pB/E1-6xHis-NANP-Met-huAmy[M35E], respectively were transformed into E. coli M15 cells already containing plasmid pREP4 by standard methods (Sambrook et al., supra). Transformed cells were grown at 37° C. in a 100 l fermenter in Super medium [Stuber et al., Immunological Methods, eds. Lefkovits and Pernis, Academic Press, Inc., Vol. IV, 121–152 [1990]] containing 100 mg/l ampicillin and 25 mg/l kanamycin. At an optical density at 600 nm of about 1.0 IPTG was added to a final concentration of 2 mM. After an additional 3 hrs at 37° C. the cells were harvested by centrifugation. In a typical fermentation run a biomass of approximately 500 g containing at least 3 g of the recombinant fusion protein was obtained.

Purification 2.5 l of 6M guanidine.HCl containing 0.1M di-sodium hydrogen phosphate, pH 8 were added to the cells and stirred for 24 hours. Crude cell debris were removed by centrifugation and the supernatant was then further clarified by cross-flow filtration using a 0.3 mm membrane. The protein contained in the filtrate was then adsorbed to a Ni-NTA column (5 cm×24 cm, flow 20 ml/min). Contaminating E.coli proteins were removed by washing first with 8M urea, pH 7.5. Elution was performed with 8M urea, pH 4. The chromatogram was monitored by SDS-PAGE and fractions containing fusion protein were pooled. A small aliquot of that pool was mixed with EDTA and desalted by dialyzing against water, lyophilized and then analyzed by electron spray mass-spectrometry (Table 1).

TABLE 1

Characterization of the fusion proteins

| Fusion Protein | Purification yield per 100 l fermenter [gram] | Theoretical mass | Average mass by electron spray MS |
|---|---|---|---|
| Human WT | 3.0 | 13817 | 13820 |
| Human Mut. M35S | 5.5 | 13773 | 13776 |
| Human Mut. M35L | 5.7 | 13799 | 13802 |
| Human Mut. M35Q | 4.5 | 13814 | 13817 |
| Human Mut. M35E | 6.0 | 13813 | not tested |
| Rat WT | 6.0 | 13724 | 13728 |

WT = wild-type, Mut = mutant, e.g. M35S (Met at position 35 is mutated to Ser)

EXAMPLE 5

Cleavage of the Fusion Proteins to Yield 1-42 β-amyloid Peptides

A semipreparative RP-18 HPLC (Vidac, specification 218TP 152010, 250 mm ×10 mm) column was first equilibrated with 8M urea, pH 4, at a flow rate of 2 ml/min. Then an aliquot of the NTA-eluate containing 400 mg fusion protein in 8M urea, pH 4, was pumped onto the column at a flow rate of 1 ml/min. Then the column was washed with 8M urea, pH 4, at a flow rate of 2 ml/min. The urea was washed out by water at a flow rate of 2 ml/min until baseline adsorbance at the column outlet was reached. Cleavage was performed by flushing the column with 45 mg/ml CNBr in a solution composed of 20% ethanol, 40% formic acid and 40% water for 24 hrs at 22° C. at a flow rate of 0.5 ml/min. The column was then flushed with 0.1M EDTA at a flow rate of 2 ml/min and CNBr together with liberated MRGSHHHHHHGS-(NANP)$_{19}$-RSM was washed out with 0.05% trifluoro acetic acid at a flow rate of 2.0 ml/min. 1-42 residue β-amyloid peptide was eluted at a flow rate of 2 ml/min using the following ethanol gradient given by the time points: (min/% ethanol) 0/0, 40/40, 45/50, 50/65, 55/100, 60/100, 65/0

Figure 6A:
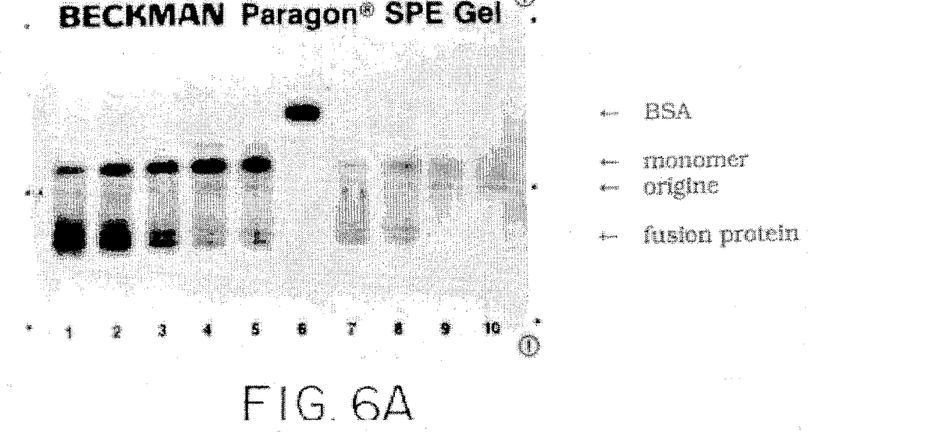
Figure 6B:
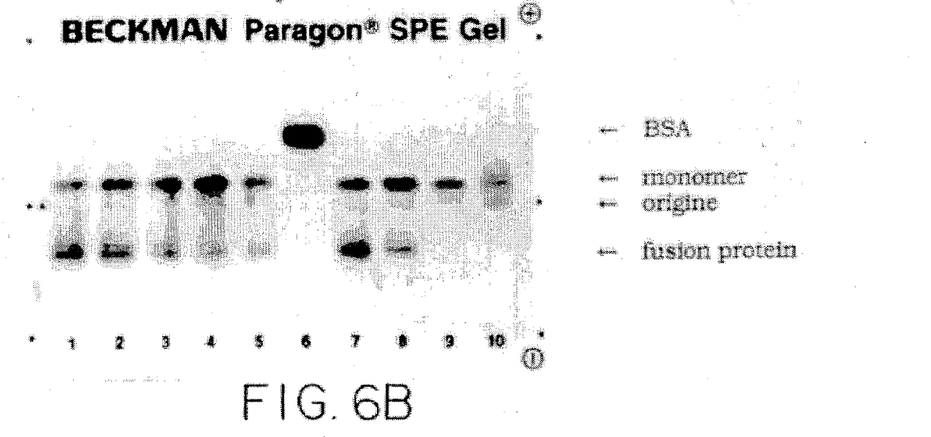
Figure 6C:
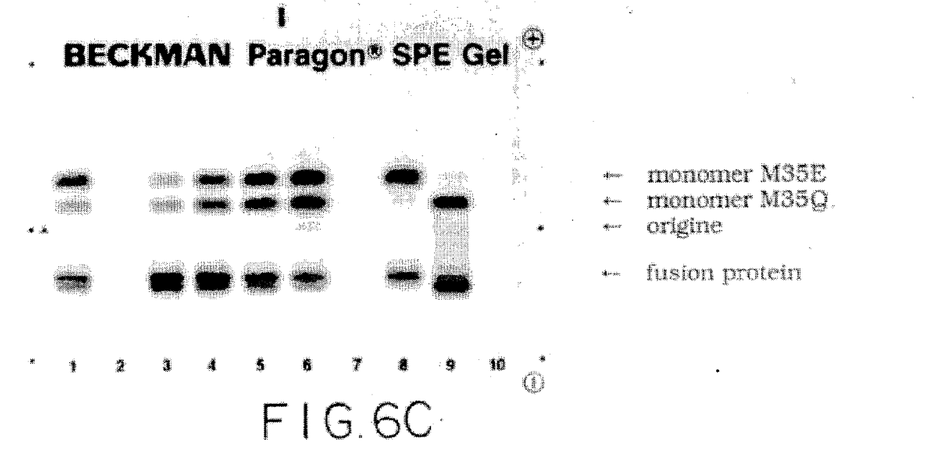
FIG. 6C—Illustrates (gel c) the results of a comparison of the point mutants M35Q bA4 and M35E bA4. Point mutant M35E bA4 contains an extra negative charge which results in a higher mobility on the Beckman gel (lane 8: M35E bA4; lane 9: M35Q bA4). When M35E bA4 is mixed with M35Q bA4 after cleavage (lane 1) or when the fusion protein containing M35Q bA4 is mixed with the fusion protein containing M35E bA4 and cleaved according to the process of the present invention (lanes 3, 4, 5 and 6 (wash 1, 2, 3 and 4)) a clear separation is observed indicating the presence of monomeric bA4.

A broad peak containing the β-amyloid peptide emerges between 45 and 60 min. Critical for the peptide to be monomeric was the immediate dilution with distilled water (e.g. by dropping the eluate into a stirred beaker containing 200 ml H$_2$O), and immediate lyophilization. The resulting powder was named W1. Since a considerable amount of β-amyloid peptide remained on the column, the elution was repeated three times using the above mentioned protocol, giving rise to samples W2, W3 and W4. These samples were tested for purity (Table 2) and the amount of monomeric bA4 (FIG. 6). The correct chemical structure of the peptides was verified by electron spray mass-spectrometry (Table 3), by amino acid analysis and by amino terminal sequencing (Table 3).

TABLE 2

Production of 1-42 β-amyloid peptides

| Peptide | Number of tests | Wash Number | Mass produced (mg) | Purity (%) |
|---|---|---|---|---|
| rat WT | 4 | 1 | 100 ± 14 | 90 ± 2 |
| (Seq ID No:2) | | 2 | 28 ± 8 | 89 ± 2 |
| | | ¾ | 9 ± 3 | 90 ± 1 |
| human WT | 3 | 1 | 96 ± 23 | 79 ± 9 |
| (Seq ID No:1) | | 2 | 52 ± 10 | 73 ± 5 |
| | | 3 | 32 ± 9 | 78 ± 4 |
| | | 4 | 15 ± 8 | 86 ± 5 |
| human M35S | 3 | 1 | 71 ± 13 | 80 ± 8 |
| (Seq ID No:4) | | 2 | 31 ± 5 | 74 ± 2 |
| | | 3 | 18 ± 7 | 83 ± 2 |
| | | 4 | 2 ± 7 | 88 ± 2 |
| human M35L | 3 | 1 | 59 ± 15 | 72 ± 8 |
| (Seq ID No:3) | | 2 | 23 ± 9 | 71 ± 4 |
| | | 3 | 8 ± 3 | 78 ± 3 |
| human M35Q | 4 | 1 | 37 ± 4 | 70 ± 2 |
| (Seq ID No:5) | | 2 | 10 ± 5 | 82 ± 3 |
| human M35E | 1 | 1 | 95 | not tested |
| (Seq ID No:6) | | 2 | 68 | not tested |
| | | 3 | 46 | not tested |
| | | 4 | 31 | not tested |

Purity is based on amino acid analysis, the content of fusion protein is detected by the quotient of Asp to Glu. Pure 1-42 β-amyloid peptide has 4 GLu and 4 Asp residues, pure fusion protein has a ratio of 42 Asp to 4 Glu.

TABLE 3

Identification of 1-42 β-amyloid peptides

| | Mass- Spectrometry | | Edman degradation |
|---|---|---|---|
| Sample | Theory | Found | 10–15 cycles |
| human WT | 4515.1 | 4531** | DAEFRHDSGYEVHHQ |
| human M35S | 4471.0 | 4472 | DAEFRHDSGY |
| human M35L | 4497.1 | 4498 | DAEFHDSGY |
| human M35Q | 4512.0 | 4512 | not tested |
| human M35E | 4513.0 | 4512 | not tested |
| rat WT | 4417.0 | 4435** | DAEFGHDSGF |

**The methionines of human WT and rat WT were transformed during the cleavage procedure to methionine sulfoxide.

EXAMPLE 6

Purification of Monomeric 1-42 bA4

Small scale method

Figure 7:
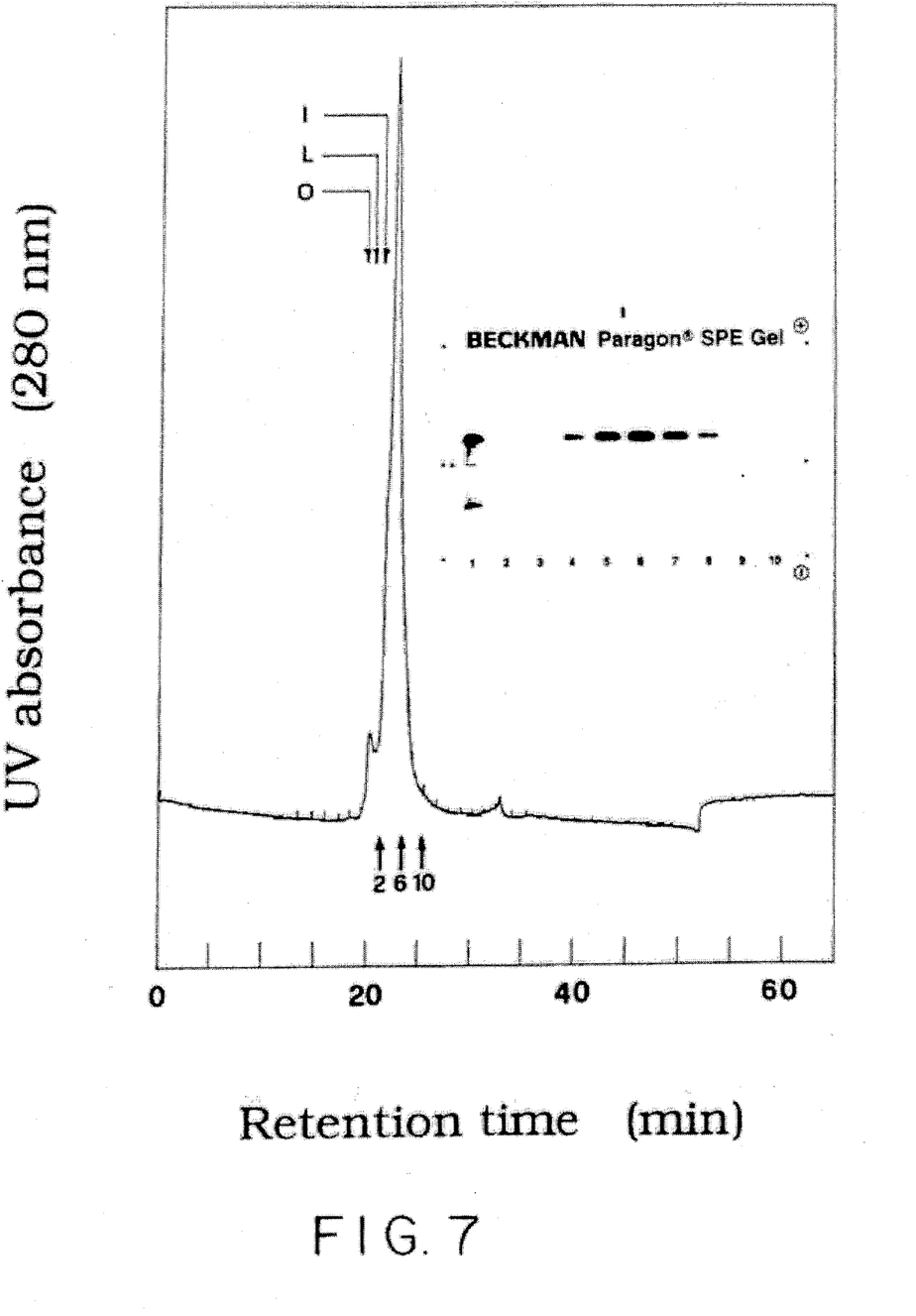
FIG. 7—Illustrates the results of bA4 chromatography on a size-exclusion column.

Samples containing 1 mg of bA4 were applied to a LKB UltroPac HPLC column (diameter: 7.5 mm, length :600 mm, flow 0.5 ml/min, buffer: 12 mM Tris(hydroxymethyl) aminomethan containing 200 mM glycine, pH 7.8). bA4 emerged in a sharp peak, and the peak fractions contained the Coomassie blue band on the agarose electrophoresis gel shown in FIG. 7. Light-scattering experiments gave no evidence of high molecular weight forms (aggregates or fibres) and calibration standards which were chromatographed under identical conditions pointed to a molecular weight of about 4500, indicating that bA4 was present as a monomer.

Preparative Scale Method

The "Continuous Elution Electrophoresis system Model 491 Prep Cell" from BioRad was used. The non-denaturating discontinuous acrylamide gel was composed of a 4% acrylamide/2.7% N,N'-methylene-bis-acrylamide separating gel in 0.375M Tris(hydroxymethyl) aminomethan (pH 8.8) with a length of 3 cm and a diameter of 37 mm, and equipped with a cooling tube of 20 mm diameter.

The stacking gel was composed of 4% acrylamide/2.7% N,N'-methylenebis-acrylamide in 0.125M Tris (hydroxymethyl)amino-methane (pH 6.8) and had a length of 2 cm. The running buffer was 25 mM Tris (hydroxymethyl)aminomethan/0.2M glycine, pH 8.3. For elution the same buffer was used with a flow rate of 0.75 ml/minutes. 45 mg of bA4 peptide, generally from wash 2, 3 or 4, were dissolved in 7 ml H$_2$O and 1 ml glycerol. Electrophoresis was performed at 12 watts (constant, limits at 500 V and 40 mA), a typical run requiring 4 hours. The results of a typical run are shown in FIG. 7.

EXAMPLE 7

Purification of 1-35 HIV-1 Peptide 400 mg fusion protein MRGS (H)$_6$ GS (NANP)$_{19}$ RSM RILA VERYLKDQQLLGIWGCSGKLICTTAVPWNAS (Seq ID No: 12) prepared and purified by the same methods as those described for the preparation and purification of the fusion proteins containing monomeric 1-42 bA4 (Examples 1–4) were loaded onto a VYDAC RP 18 column (specification 218 TP 152010, 250 mm×10 mm) and cleaved using the same conditions as those described for the cleavage of the 1-42 bA4 fusion proteins (Example 5). Approximately 20–30 mg of lyophilized powder were obtained. This powder was analyzed by electron spray analysis. A peak of 3902±2 Da corresponding to the 1-35 HIV-1 peptide (Seq ID No: 11) was detected.

The present invention has been described in terms of its preferred embodiments. However, after reading the present specification various alternative embodiments will become apparent to those skilled in the art.

These variations are to be considered within the scope and spirit of the subject invention, which is only to be limited by the claims which follow and their equivalents.

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 42 amino acids
        ( B ) TYPE: amino acid
        ( D ) TOPOLOGY: linear     ( i i ) MOLECULE TYPE: peptide     ( v ) FRAGMENT TYPE: N-terminal     ( x i ) SEQUENCE DESCRIPTION: SEQ ID NO: 1:

```
Asp Ala Glu Phe Arg His Asp Ser Gly Tyr Glu Val His His Gln Lys
 1               5                  10                    15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```

( 2 ) INFORMATION FOR SEQ ID NO: 2:

( i ) SEQUENCE CHARACTERISTICS:
        ( A ) LENGTH: 42 amino acids
        ( B ) TYPE: amino acid
        ( D ) TOPOLOGY: linear     ( i i ) MOLECULE TYPE: peptide     ( v ) FRAGMENT TYPE: N-terminal     ( x i ) SEQUENCE DESCRIPTION: SEQ ID NO: 2:

```
Asp Ala Glu Phe Gly His Asp Ser Gly Phe Glu Val Arg His Gln Lys
 1               5                  10                    15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```

( 2 ) INFORMATION FOR SEQ ID NO: 3:

( i ) SEQUENCE CHARACTERISTICS:
        ( A ) LENGTH: 42 amino acids
        ( B ) TYPE: amino acid
        ( D ) TOPOLOGY: linear     ( i i ) MOLECULE TYPE: peptide     ( v ) FRAGMENT TYPE: N-terminal     ( x i ) SEQUENCE DESCRIPTION: SEQ ID NO: 3:

```
Asp Ala Glu Phe Arg His Asp Ser Gly Tyr Glu Val His His Gln Lys
 1               5                  10                    15

Leu Val Phe Phe Ala Glu Asp Val Gly Ser Asn Lys Gly Ala Ile Ile
            20                  25                  30
```

```
Gly  Leu  Leu  Val  Gly  Gly  Val  Val  Ile  Ala
          35                  40
```

(2) INFORMATION FOR SEQ ID NO: 4:

(i) SEQUENCE CHARACTERISTICS:
    (A) LENGTH: 42 amino acids
    (B) TYPE: amino acid
    (D) TOPOLOGY: linear (ii) MOLECULE TYPE: peptide (v) FRAGMENT TYPE: N-terminal (xi) SEQUENCE DESCRIPTION: SEQ ID NO: 4:

```
Asp  Ala  Glu  Phe  Arg  His  Asp  Ser  Gly  Tyr  Glu  Val  His  His  Gln  Lys
1                   5                   10                      15

Leu  Val  Phe  Phe  Ala  Glu  Asp  Val  Gly  Ser  Asn  Lys  Gly  Ala  Ile  Ile
               20                  25                      30

Gly  Leu  Ser  Val  Gly  Gly  Val  Val  Ile  Ala
          35                  40
```

(2) INFORMATION FOR SEQ ID NO: 5:

(i) SEQUENCE CHARACTERISTICS:
    (A) LENGTH: 42 amino acids
    (B) TYPE: amino acid
    (D) TOPOLOGY: linear (ii) MOLECULE TYPE: peptide (v) FRAGMENT TYPE: N-terminal (xi) SEQUENCE DESCRIPTION: SEQ ID NO: 5:

```
Asp  Ala  Glu  Phe  Arg  His  Asp  Ser  Gly  Tyr  Glu  Val  His  His  Gln  Lys
1                   5                   10                      15

Leu  Val  Phe  Phe  Ala  Glu  Asp  Val  Gly  Ser  Asn  Lys  Gly  Ala  Ile  Ile
               20                  25                      30

Gly  Leu  Gln  Val  Gly  Gly  Val  Val  Ile  Ala
          35                  40
```

(2) INFORMATION FOR SEQ ID NO: 6:

(i) SEQUENCE CHARACTERISTICS:
    (A) LENGTH: 42 amino acids
    (B) TYPE: amino acid
    (D) TOPOLOGY: linear (ii) MOLECULE TYPE: peptide (v) FRAGMENT TYPE: N-terminal (xi) SEQUENCE DESCRIPTION: SEQ ID NO: 6:

```
Asp  Ala  Glu  Phe  Arg  His  Asp  Ser  Gly  Tyr  Glu  Val  His  His  Gln  Lys
1                   5                   10                      15

Leu  Val  Phe  Phe  Ala  Glu  Asp  Val  Gly  Ser  Asn  Lys  Gly  Ala  Ile  Ile
               20                  25                      30

Gly  Leu  Glu  Val  Gly  Gly  Val  Val  Ile  Ala
          35                  40
```

(2) INFORMATION FOR SEQ ID NO: 7:

(i) SEQUENCE CHARACTERISTICS:
    (A) LENGTH: 520 base pairs
    (B) TYPE: nucleic acid
    (C) STRANDEDNESS: single
    (D) TOPOLOGY: linear ( i i ) MOLECULE TYPE: DNA (genomic)

( i x ) FEATURE:
    ( A ) NAME/KEY: CDS
    ( B ) LOCATION: 115..516
    ( D ) OTHER INFORMATION: /product="Amyloid Protein AA"

( x i ) SEQUENCE DESCRIPTION: SEQ ID NO: 7:

```
CTCGAGAAAT CATAAAAAAT TTATTTGCTT TGTGAGCGGA TAACAATTAT AATAGATTCA           60

ATTGTGAGCG GATAACAATT TCACACAGAA TTCATTAAAG AGGAGAAATT AACT ATG           117
                                                               Met
                                                                1

AGA GGA TCG CAT CAC CAT CAC CAT CAC GGA TCT AAC GCG AAC CCG AAC           165
Arg Gly Ser His His His His His His Gly Ser Asn Ala Asn Pro Asn
              5               10                  15

GCG AAC CCG AAC GCG AAC CCG AAC GCG AAC CCG AAC GCG AAC CCG AAC           213
Ala Asn Pro Asn Ala Asn Pro Asn Ala Asn Pro Asn Ala Asn Pro Asn
         20                  25                  30

GCG AAC CCG AAC GCG AAC CCG AAC GCG AAC CCG AAC GCG AAC CCG AAC           261
Ala Asn Pro Asn Ala Asn Pro Asn Ala Asn Pro Asn Ala Asn Pro Asn
     35                      40                  45

GCG AAC CCG AAC GCG AAC CCG AAC GCG AAC CCG AAC GCG AAC CCG AAC           309
Ala Asn Pro Asn Ala Asn Pro Asn Ala Asn Pro Asn Ala Asn Pro Asn
 50                      55                  60                  65

GCG AAC CCG AAC GCG AAC CCG AAC GCG AAC CCG AAC GCG AAC CCG AAC           357
Ala Asn Pro Asn Ala Asn Pro Asn Ala Asn Pro Asn Ala Asn Pro Asn
                 70                  75                  80

GCG AAC CCG AAC GCG AAC CCG AGA TCT ATG GAT GCG GAG TTC GGA CAT           405
Ala Asn Pro Asn Ala Asn Pro Arg Ser Met Asp Ala Glu Phe Gly His
             85                  90                  95

GAT TCA GGC TTC GAA GTC CGC CAT CAA AAA CTG GTG TTC TTT GCA GAA           453
Asp Ser Gly Phe Glu Val Arg His Gln Lys Leu Val Phe Phe Ala Glu
         100                 105                 110

GAT GTG GGT TCA AAC AAA GGT GCC ATC ATT GGA CTC ATG GTG GGT GGC           501
Asp Val Gly Ser Asn Lys Gly Ala Ile Ile Gly Leu Met Val Gly Gly
     115                     120                 125

GTT GTC ATA GCA TAAGCTT                                                   520
Val Val Ile Ala
130
```

( 2 ) INFORMATION FOR SEQ ID NO: 8:

( i ) SEQUENCE CHARACTERISTICS:
        ( A ) LENGTH: 133 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 8:

```
Met Arg Gly Ser His His His His His His Gly Ser Asn Ala Asn Pro
 1               5                   10                  15

Asn Ala Asn Pro Asn Ala Asn Pro Asn Ala Asn Pro Asn Ala Asn Pro
             20                  25                  30

Asn Ala Asn Pro Asn Ala Asn Pro Asn Ala Asn Pro Asn Ala Asn Pro
         35                  40                  45

Asn Ala Asn Pro Asn Ala Asn Pro Asn Ala Asn Pro Asn Ala Asn Pro
     50                  55                      60

Asn Ala Asn Pro Asn Ala Asn Pro Asn Ala Asn Pro Asn Ala Asn Pro
 65                  70                  75                  80

Asn Ala Asn Pro Asn Ala Asn Pro Arg Ser Met Asp Ala Glu Phe Gly
```

|   |   |   |   |   | 85 |   |   |   |   | 90 |   |   |   |   | 95 |   |   |
|---|---|---|---|---|----|---|---|---|---|----|---|---|---|---|----|---|---|

His Asp Ser Gly Phe Glu Val Arg His Gln Lys Leu Val Phe Phe Ala
          100                   105                  110

Glu Asp Val Gly Ser Asn Lys Gly Ala Ile Ile Gly Leu Met Val Gly
        115                   120                 125

Gly Val Val Ile Ala
130

( 2 ) INFORMATION FOR SEQ ID NO: 9:

( i ) SEQUENCE CHARACTERISTICS:
        ( A ) LENGTH: 520 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 115..516
        ( D ) OTHER INFORMATION: /product="Amyloid Protein AA"

( x i ) SEQUENCE DESCRIPTION: SEQ ID NO: 9:

CTCGAGAAAT CATAAAAAAT TTATTTGCTT TGTGAGCGGA TAACAATTAT AATAGATTCA    60

ATTGTGAGCG GATAACAATT TCACACAGAA TTCATTAAAG AGGAGAAATT AACT ATG   117
                                                                                      Met
                                                                                      1

AGA GGA TCG CAT CAC CAT CAC CAT CAC GGA TCT AAC GCG AAC CCG AAC   165
Arg Gly Ser His His His His His His Gly Ser Asn Ala Asn Pro Asn
              5                                10                          15

GCG AAC CCG AAC GCG AAC CCG AAC GCG AAC CCG AAC GCG AAC CCG AAC   213
Ala Asn Pro Asn Ala Asn Pro Asn Ala Asn Pro Asn Ala Asn Pro Asn
        20                         25                       30

GCG AAC CCG AAC GCG AAC CCG AAC GCG AAC CCG AAC GCG AAC CCG AAC   261
Ala Asn Pro Asn Ala Asn Pro Asn Ala Asn Pro Asn Ala Asn Pro Asn
        35                         40                       45

GCG AAC CCG AAC GCG AAC CCG AAC GCG AAC CCG AAC GCG AAC CCG AAC   309
Ala Asn Pro Asn Ala Asn Pro Asn Ala Asn Pro Asn Ala Asn Pro Asn
50                         55                         60                     65

GCG AAC CCG AAC GCG AAC CCG AAC GCG AAC CCG AAC GCG AAC CCG AAC   357
Ala Asn Pro Asn Ala Asn Pro Asn Ala Asn Pro Asn Ala Asn Pro Asn
        70                         75                       80

GCG AAC CCG AAC GCG AAC CCG AGA TCT ATG GAT GCG GAG TTC CGT CAT   405
Ala Asn Pro Asn Ala Asn Pro Arg Ser Met Asp Ala Glu Phe Arg His
        85                         90                       95

GAT TCA GGC TAT GAA GTC CAC CAT CAA AAA CTG GTG TTC TTT GCA GAA   453
Asp Ser Gly Tyr Glu Val His His Gln Lys Leu Val Phe Phe Ala Glu
        100                      105                     110

GAT GTG GGT TCA AAC AAA GGT GCC ATC ATT GGA CTC ATG GTG GGT GGC   501
Asp Val Gly Ser Asn Lys Gly Ala Ile Ile Gly Leu Met Val Gly Gly
        115                      120                     125

GTT GTC ATA GCA TAAGCTT   520
Val Val Ile Ala
130

( 2 ) INFORMATION FOR SEQ ID NO: 10:

( i ) SEQUENCE CHARACTERISTICS:
        ( A ) LENGTH: 133 amino acids
        ( B ) TYPE: amino acid
        ( D ) TOPOLOGY: linear     ( i i ) MOLECULE TYPE: protein ( x i ) SEQUENCE DESCRIPTION: SEQ ID NO: 10:

```
Met Arg Gly Ser His His His His His Gly Ser Asn Ala Asn Pro
 1               5                   10                  15

Asn Ala Asn Pro Asn Ala Asn Pro Asn Ala Asn Pro Asn Ala Asn Pro
            20              25              30

Asn Ala Asn Pro Asn Ala Asn Pro Asn Ala Asn Pro Asn Ala Asn Pro
            35              40              45

Asn Ala Asn Pro Asn Ala Asn Pro Asn Ala Asn Pro Asn Ala Asn Pro
 50                  55                  60

Asn Ala Asn Pro Asn Ala Asn Pro Asn Ala Asn Pro Asn Ala Asn Pro
 65              70                  75                  80

Asn Ala Asn Pro Asn Ala Asn Pro Arg Ser Met Asp Ala Glu Phe Arg
                 85              90                  95

His Asp Ser Gly Tyr Glu Val His His Gln Lys Leu Val Phe Phe Ala
             100             105                 110

Glu Asp Val Gly Ser Asn Lys Gly Ala Ile Ile Gly Leu Met Val Gly
         115             120                 125

Gly Val Val Ile Ala
        130
```

( 2 ) INFORMATION FOR SEQ ID NO: 11:

( i ) SEQUENCE CHARACTERISTICS:
        ( A ) LENGTH: 35 amino acids
        ( B ) TYPE: amino acid
        ( D ) TOPOLOGY: linear     ( i i ) MOLECULE TYPE: peptide ( x i ) SEQUENCE DESCRIPTION: SEQ ID NO: 11:

```
Arg Ile Leu Ala Val Glu Arg Tyr Leu Lys Asp Gln Gln Leu Leu Gly
 1               5                   10                  15

Ile Trp Gly Cys Ser Gly Lys Leu Ile Cys Thr Thr Ala Val Pro Trp
             20              25                  30

Asn Ala Ser
        35
```

( 2 ) INFORMATION FOR SEQ ID NO: 12:

( i ) SEQUENCE CHARACTERISTICS:
        ( A ) LENGTH: 126 amino acids
        ( B ) TYPE: amino acid
        ( D ) TOPOLOGY: linear     ( i i ) MOLECULE TYPE: protein ( x i ) SEQUENCE DESCRIPTION: SEQ ID NO: 12:

```
Met Arg Gly Ser His His His His His His Gly Ser Asn Ala Asn Pro
 1               5                   10                  15

Asn Ala Asn Pro Asn Ala Asn Pro Asn Ala Asn Pro Asn Ala Asn Pro
            20              25              30

Asn Ala Asn Pro Asn Ala Asn Pro Asn Ala Asn Pro Asn Ala Asn Pro
            35              40              45

Asn Ala Asn Pro Asn Ala Asn Pro Asn Ala Asn Pro Asn Ala Asn Pro
 50                  55                  60

Asn Ala Asn Pro Asn Ala Asn Pro Asn Ala Asn Pro Asn Ala Asn Pro
 65              70                  75                  80

Asn Ala Asn Pro Asn Ala Asn Pro Arg Ser Met Arg Ile Leu Ala Val
                 85              90                  95
```

| | | | | | | | | | | | | | | |
|---|---|---|---|---|---|---|---|---|---|---|---|---|---|---|
| Glu | Arg | Tyr | Leu<br>100 | Lys | Asp | Gln | Gln | Leu<br>105 | Leu | Gly | Ile | Trp | Gly<br>110 | Cys | Ser |
| | Gly | Lys | Leu<br>115 | Ile | Cys | Thr | Thr | Ala<br>120 | Val | Pro | Trp | Asn | Ala<br>125 | Ser | |

What is claimed is:

1. A process for production and purification of a desired hydrophobic polypeptide, protein or peptide, which comprises:

a) passing an aqueous solution containing a fusion protein of the formula:

A—B—C wherein A is a hydrophilic peptide comprising (NANP)$_X$, X is from 10 to 40, B is a selective cleavage site, and C is a desired hydrophobic polypeptide, protein or peptide through a hydrophobic matrix column, b) flushing the column with a solution containing a cleavage reagent or an enzyme; and c) removing the resulting desired hydrophobic polypeptide, protein or peptide with an aqueous water miscible solvent.

2. A process in accordance with claim 1, wherein the hydrophobic matrix column is an octadecyl bound silica microparticle column.

3. A process in accordance with claim 1, wherein the cleavage reagent is cyanogen bromide.

4. A process for producing monomeric β-amyloid peptide, which comprises:

a) passing an aqueous solution containing a fusion protein of the formula:

A—B—C wherein A is a hydrophilic peptide comprising (NANP)$_X$, X is from 10 to 40, B is a selective cleavage site, and C is a desired hydrophobic polypeptide, protein or peptide, wherein the desired hydrophobic polypeptide is β-amyloid peptide or a point mutant of β-amyloid peptide having at position 35 a leucine, serine, glutamine; or glutamic acid residue instead of a methionine or methionine sulfoxide residue through a hydrophobic matrix column, b) flushing the column with a solution containing a cleavage reagent or an enzyme, c) obtaining monomeric β-amyloid peptide by elution with an aqueous water solvent, and d) diluting the monomeric β-amyloid peptide with distilled water followed by lyophilization.

5. A process in accordance with claim 4, further comprising purifying the monomeric β-amyloid peptide after lyophilization to achieve protein homogeneity.

6. A process in accordance with claim 4, wherein the hydrophobic matrix column is an octadecyl bound silica microparticle column.

7. A process in accordance with claim 4, wherein the cleavage reagent is cyanogen bromide.

8. A process in accordance with claim 1, wherein the desired hydrophobic polypeptide, protein or peptide is the 1-35 HIV-1 peptide.

* * * * *